(12) United States Patent
Kaelin

(10) Patent No.: US 11,672,706 B2
(45) Date of Patent: Jun. 13, 2023

(54) ENHANCED ADHESIVE LENS COVER SET AND GASKET THEREFOR

(71) Applicant: Dylan Kaelin, Beaver County (CA)

(72) Inventor: Dylan Kaelin, Beaver County (CA)

( * ) Notice: Subject to any disclaimer, the term of this patent is extended or adjusted under 35 U.S.C. 154(b) by 0 days.

(21) Appl. No.: 17/619,675

(22) PCT Filed: Nov. 23, 2020

(86) PCT No.: PCT/CA2020/051591
§ 371 (c)(1),
(2) Date: Jun. 14, 2022

(87) PCT Pub. No.: WO2022/104447
PCT Pub. Date: May 27, 2022

(65) Prior Publication Data
US 2022/0370247 A1    Nov. 24, 2022

(51) Int. Cl.
*A61F 9/02* (2006.01)
(52) U.S. Cl.
CPC .................... *A61F 9/025* (2013.01)
(58) Field of Classification Search
CPC .................. A61F 9/025; A61F 9/029
See application file for complete search history.

(56) References Cited

U.S. PATENT DOCUMENTS

| 4,076,373 A * | 2/1978 | Moretti | A61F 9/025 |
| | | | 359/507 |
| 4,138,746 A * | 2/1979 | Bergmann | A42B 3/26 |
| | | | 2/10 |
| 4,455,689 A * | 6/1984 | Boyer | A61F 9/025 |
| | | | 2/434 |
| 4,563,065 A * | 1/1986 | Kreissl | G02C 7/086 |
| | | | 351/86 |
| 4,716,601 A * | 1/1988 | McNeal | A61F 9/025 |
| | | | 2/434 |
| 9,161,858 B2 * | 10/2015 | Capers | A42B 3/26 |
| 9,295,297 B2 * | 3/2016 | Wilson | A61F 9/025 |
| 9,442,306 B1 * | 9/2016 | Hines | G06F 3/00 |
| 9,918,876 B2 * | 3/2018 | Wilson | A61F 9/025 |
| 10,321,731 B2 * | 6/2019 | Wilson | A61F 9/025 |
| 10,342,704 B2 * | 7/2019 | Blanchard | A61F 9/028 |

(Continued)

FOREIGN PATENT DOCUMENTS

| EP | 2890341 A2 | 7/2015 |
| EP | 3646829 A1 | 5/2020 |

OTHER PUBLICATIONS

International Search Report and Written Opinion dated Aug. 2, 2021 for PCT/CA2020/051591.

*Primary Examiner* — F Griffin Hall
(74) *Attorney, Agent, or Firm* — Suiter Swantz pc llo

(57) ABSTRACT

An enhanced adhesive lens cover set for use with a wearable viewing lens such as goggles or a helmet. The lens includes alignment means in proximity to the outer circumference. The laminated plurality of disposable lens covers has a pliable gasket disposed on a rearward surface thereof for adhesive attachment to the viewing lens inside of the alignment means. A releasable gasket for use with a prior art lens cover set is also disclosed. The gasket is of a deformable thickness, to minimize the likelihood of a breach of the circumferential seal between the lens cover set and the viewing lens when the disposable lens covers are peeled away.

13 Claims, 6 Drawing Sheets

(56) References Cited

U.S. PATENT DOCUMENTS

| | | | |
|---|---|---|---|
| 10,675,185 B2* | 6/2020 | Garcia | A61F 9/027 |
| 11,013,636 B2* | 5/2021 | Sigismondo | A61F 9/025 |
| 2012/0137414 A1* | 6/2012 | Saylor | B32B 27/00 |
| | | | 428/80 |
| 2014/0057074 A1* | 2/2014 | Mcinturff | A61F 9/025 |
| | | | 428/131 |
| 2014/0063438 A1* | 3/2014 | Cater | G02C 5/12 |
| | | | 351/62 |

\* cited by examiner

ENHANCED ADHESIVE LENS COVER SET AND GASKET THEREFOR

FIELD OF THE INVENTION

This invention is in the field of vision enhancement and protection equipment for use in rugged outdoor applications and the like, and more specifically relates to an enhanced method of attachment of a disposable lens cover set to a wearable viewing lens, using a gasket of deformable thickness, enhancing the circumferential seal therebetween and eliminating avenues of ingress of debris and moisture.

BACKGROUND OF THE INVENTION

In certain rugged applications, such as motocross riding and other outdoor sports or work applications, the ability to rapidly clean a visor or lens from the visibility perspective is important. In many such applications, a system which is used is that of a plurality of peel-away lens covers which are adhesively attached to the outer viewing surface of a viewing lens which can be rapidly peeled away for cleaning purposes during use or operation.

Configuration and attachment of these disposable lens covers to the front of the viewing lands on a helmet, goggles of the like often incorporates reliance upon alignment means extending forward from the viewing lens—retaining posts or the like. Retaining posts are disposed around the perimeter of the viewing area or the outer circumference of the viewing lens itself which can extend through one or more holes in the disposable lens covers to allow for their rapid alignment and consistent attachment.

One of the shortcomings of the current state of the art with respect to disposable lens cover sets which are used on viewing lenses for helmets, goggles and the like in these applications is the likelihood as the peel-away lens covers are removed for a breach in the seal around the edge of the lens cover set resulting in the ability for ingress of debris, moisture and the like between the lens and the lens covers. If it were possible to provide a means of attachment of a multiple of removable lens covers that would incorporate a circumferential seal between the covers and the lens surface itself, the circumferential seal could minimize the likelihood of entrance of any moisture or debris there in and maximize the visibility in the lens.

Problems in prior attempts include the fact that the peel-away lens covers themselves are insufficiently adhered to reliably stick to the front surface of the lens when one or more layers are being removed from a plurality thereof. If it were possible to provide a system maximizing the adhesive nature of the disposable lens cover set, while still permitting for its releasable attachment, it is contemplated that this would be well received commercially.

SUMMARY OF THE INVENTION

The invention comprises a lens cover set for use on the outward surface of a viewing lens, which includes a seal enhancing gasket on the rearward face thereof, as well as a gasket for use to provide enhanced adhesive attachment of a lens cover set to an outward surface of a wearable viewing lens. The gasket is made of a material of deformable thickness which permits stretching and variation in the thickness of the gasket, and the outer circumference of the gasket is shaped to be placed inside of the perimeter defined by alignment means on the face of the viewing lens.

In a first embodiment, the present invention comprises a gasket for use to provide enhanced adhesive attachment of a lens cover set to an outward surface of a wearable viewing lens. The lens cover set itself would comprise a plurality of adhesively laminated disposable lens covers.

The lens cover set is transparent and see-through in nature, and each of the disposable lens covers has an outward facing surface which is nonadhesive to provide a clean outer vision surface, and an inward facing surface including a releasable adhesive to allow laminar attachment to the outward facing surface of the adjacent optical lens cover in the lens cover set.

The wearable viewing lens has alignment means extending outwards therefrom in proximity to the outer circumference of the viewing lens, to facilitate the alignment of the lens cover set in relation to the wearable viewing lens. The alignment means define a viewing perimeter.

The inward facing surface of the innermost disposable lens cover of the lens cover set permits adhesive attachment of the lens cover set to the outward surface of the viewing lens, and the lens cover set is of a size approximately corresponding to the outer circumference of the lens. The lens cover set, by virtue of its transparent see-through nature, provides a clear vision surface on the outer surface of the wearable viewing lens.

The lens cover set will engage the alignment means, to permit alignment of the lens cover set to the viewing lens during any adhesive attachment thereof. The adhesion value of the releasable adhesive between the disposable lens covers of the lens cover set will permit the peel-away removal of the outward most disposable lens cover of the lens cover set for disposal, when the visibility therethrough is impaired.

The gasket itself comprises a material of deformable thickness which permits stretching and variation in the thickness of the gasket. The gasket has a front surface and a rear surface. The outer circumference of the rear surface of the gasket includes a releasable adhesive for attachment to the outward surface of the viewing lens. The front surface of the gasket will permit adhesive engagement of the inward facing adhesive surface of the innermost disposable lens cover of the lens cover set, to provide a circumferential seal between the lens cover set and the viewing lens preventing the entry of moisture or debris between the lens cover set and the viewing lens. The gasket is sized and shaped to fit within the viewing perimeter defined by the alignment means on the face of the lens, such that the circumferential seal created by the gasket between the lens cover set in the viewing lens is positioned inside of the alignment means. By making the gasket be of an appropriate shape and size to be positioned inside of the alignment means on the front surface of the viewing lens, the adhesive ability of the gasket is maximized and the likelihood of negatively impacting or breaching the circumferential seal created by the gasket upon the peel-away removal of one or more disposable lens covers from the lens cover set is minimized.

The adhesion value of the adhesive used to attach the gasket between the lens cover set and the viewing lens, on the rear surface of the gasket, is higher than the adhesion value of the adhesive between the disposable lens covers of the lens cover set, whereby the gasket will not pull away from the surface of the viewing lens when the laminated disposable lens covers are removed from the front of the viewing lens.

When the front surface of the gasket is pulled on by an adhesively attached lens cover set, the thickness of the gasket will deform thus maintaining the circumferential seal until the pulling force on the lens cover set is sufficient to release the lens cover set from the front surface of the gasket.

The gasket of the present invention could be used with multiple types of viewing lenses and alignment means. Many different types of viewing shields or lens surfaces will be understood to those skilled in the art and the alignment means could comprise really any type of an attachment or alignment mechanism which would result in the ability to align the disposable lens cover set in relation to the viewing lens surface. It is specifically contemplated that the alignment means could comprise a plurality of retaining posts extending outwards from the outer surface of the viewing lens in proximity to the outer circumference thereof, which are used to engage corresponding apertures extending through the lens cover set. Any type of alignment means capable of engaging a corresponding mechanism or aperture or the like of a lens cover set to permit the alignment thereof with the lens surface will be understood to be within the scope of the present invention.

The gasket could be manufactured of any type of a pliable polymeric material which was deformable, for the purpose of providing the maximum level of circumferential seal between the lens cover set and the viewing lens surface when combined therewith and permitting the stretching and variation in the thickness of the gasket as it is pulled on by an adhesively attached lens cover set. Different types of polymeric material of manufacture will all be understood to those skilled in the art and are all intended to be within the scope of the present invention.

Many different types of disposable lens covers and lens cover sets are known in the prior art which do not incorporate at this point a deformable gasket such as that disclosed for placement on the outer surface of the viewing lens inside of the alignment means. Any type of lens cover set or plurality of disposable lens covers laminated to each other such as outlined herein will be understood to be within the scope of the present invention, including lens cover sets and disposable lens covers which include nonadhesive gripping means for manual gripping and adhesive release thereof from the lens cover set.

The gasket of the present invention could also be used between multiple lens cover sets attached via and in relation to the alignment means on the outer surface of a wearable viewing lens and this will also be understood to be within the scope of the present invention.

The gasket of the present invention might be manufactured including a nonadhesive protective covering removably attached to the adhesive rear surface of the gasket, such that the nonadhesive protective covering could be removed or peeled away when the gasket was to be attached to the lens surface. Nonadhesive protective coverings for use on adhesive surfaces, such as a peel-away paper or the like, can be manufactured using many different types of materials all of which will be understood to those skilled in the art and are intended again to be within the scope of the present invention.

Certain embodiments of the gasket of the present invention might also include an adhesive front surface, facing outward when the gasket is positioned in relation to the viewing lens, and permitting and enhanced adhesive attachment between the front surface of the gasket and a lens cover set aligned therewith.

As outlined, the outer shape of the gasket, being such that it can be applied in relation to the viewing perimeter and inside of the alignment means on the face of the lens, and the deformable nature of the material manufacture of the gasket in combination with the adhesive used to attach it to the lens, render the gasket and the combination of the gasket with the laminated lens covers, novel over the prior art. The deformable nature and adhesion value of the adhesive used result in the ability for the gasket to deform and scratch as required and within reason maintain the circumferential seal created by the gasket in relation to the attachment of the lens covers to the lens surface.

In addition to the deformable gasket of the present invention which could be used with a lens cover set for use on outward surface of the viewing lens, the present invention also comprises a lens cover set for use on outward surface of the viewing lens with an integral deformable gasket in accordance with the remainder of the present invention. The lens cover set of the present invention, for use on outward surface of the viewing lens having alignment means extending outwards therefrom in proximity to the outer circumference of the viewing lens, would comprise a plurality of adhesively laminated disposable lens covers, laminated together. Each of the disposable lens covers has outward facing surface which is nonadhesive in nature and provides a clean outer vision surface, and then inward facing surface including a releasable adhesive which allows laminated attachment to the outward facing surface of the adjacent optical lens cover in the lens cover set. The adhesion value of the releasable adhesive between the disposable lens covers of the lens cover set will permit the peel-away removal of the outward most disposable lens cover of the lens cover set for disposal when the visibility therethrough is impaired. The disposable lens covers and the adhesive therebetween are visibly transparent, to provide a clear vision surface when the lens cover sets attached to the outward facing surface of a wearable viewing lens.

The lens cover set also includes a deformable gasket having a front surface and rear surface, the rear surface thereof being capable of adhesive attachment to the outward surface at the viewing lens, inside the positions of the alignment means on the viewing lens. The rear surface of the gasket includes a releasable adhesive for attachment of the gasket to the outward surface of the viewing lens and the front surface of the gasket will, when attached to the outward surface of the viewing lens, permit adhesive engagement of the inward-facing adhesive surface of the innermost disposable lens cover of the lens cover set to provide a circumferential seal between the lens cover set and the viewing lens preventing the entry of moisture or debris between the lens cover set and the viewing lens. By virtue of the deformable material of manufacture of the gasket, the gasket can be stretched and varied in its thickness when a pulling motion is applied to the front surface, allowing for a maximized circumferential seal behaviour being created and maintained by the gasket as the peel-away lens covers are removed.

The gasket is sized and shaped such that it will be positionable within the outer circumference of the viewing lens and inside of the positions of the alignment means on the viewing lens, whereby the circumferential seal created by the gasket between the lens cover set in the viewing lens is positioned inside of the alignment means. Different gaskets could be manufactured for use with lens cover sets having different shaped and sized wearable lens cover surfaces, or the gaskets could also be manufactured in a way that they would interchangeably be usable with multiple viewing lenses having a range of outer circumferences and sizes.

The inward facing surface of the innermost disposable lens cover of the lens cover set would permit the adhesive attachment of the lens cover set to the outward surface of the viewing lens.

The size of the lens cover set and the individual disposable lens covers correspond approximately to the outer circumferential size of the viewing lens in respect of which the lens cover set is to be, and the combination of the disposable lens covers and their laminating adhesive are clear such that the lens cover set when attached to the lands maintains the transparency through nature thereof. The lens cover set will also engage the alignment means permit alignment of the lens cover set to the viewing lens during any adhesive attachment. Many different types of approaches can be taken to permit the coordination of the alignment means on the surface of the lands and the adhesively attachable lens cover set, including the alignment means comprising a plurality of posts extending outwards from the front surface of the viewing lens in proximity to the outer circumference thereof, corresponding to apertures extending through the disposable lens cover set.

The lens cover set might further comprise a corresponding plurality of apertures or holes therethrough which could be used to specifically engage alignment means such as retaining posts extending forward from the outward surface of the viewing lens, permitting the alignment of the lens cover set with the lens surface as it is adhesively attached. Any type of apertures or other corresponding alignment receptacles on or through the lens cover set which are capable of engagement of alignment means on the outer surface of the viewing lines will be understood to be within the scope of the present invention.

The optical lens covers of the lens cover set could include nonadhesive gripping means, such as a tab or the like, for manual gripping by the user and used to streamline the removal thereof from the set.

The alignment means of the lens cover could extend sufficiently forward from the viewing lens to permit the stacked attachment of multiple lens cover sets on top of each other, allowing the user to maximize the number of disposable lens covers available on the lens surface at one time.

The wearable viewing lens could be any type of a viewing lens in which the need existed to provide the ability to have a removable or disposable lens covered on the front thereof, with an enhanced circumferential seal between the lens and the cover, and could specifically include goggles or a helmet used in rugged outdoor applications such as motocross or the like where it was desired to limit the ability for the entrance of debris or moisture onto the front of the viewing lens of the goggles or helmet behind the disposable cover, and by including or using disposable covers providing the ability to rapidly and cleanly remove debris from the front of the wearable lens. Any type of a wearable viewing lens for use in similar ultimate applications will be understood to be within the scope of the intended coverage of the present invention.

DESCRIPTION OF THE DRAWINGS

To easily identify the discussion of any particular element or act, the most significant digit or digits in a reference number refer to the figure number in which that element is first introduced. The drawings enclosed are.

DETAILED DESCRIPTION OF ILLUSTRATED EMBODIMENTS

Figure 1:
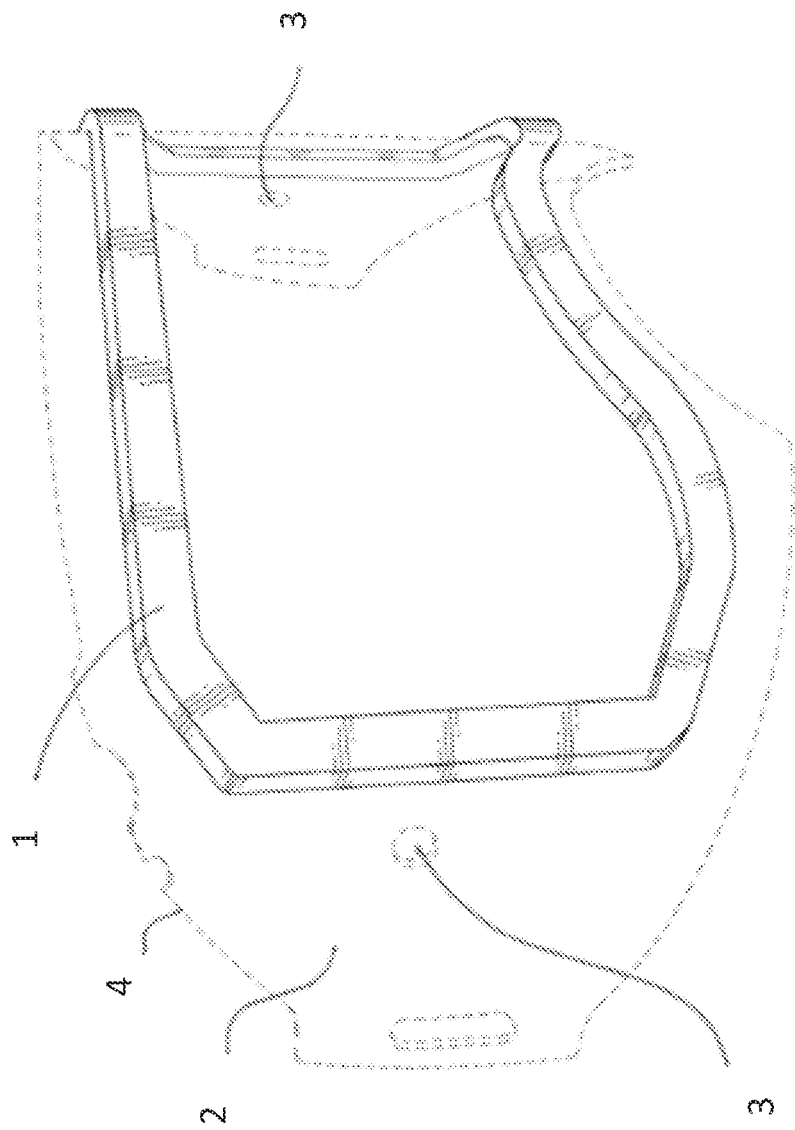
FIG. 1 is a perspective view of one embodiment of the deformable gasket of the present invention, with the outer outline of the viewing lens surface shown in dotted outline.

We will now describe the illustrated embodiments of the invention in further detail. Referring first to FIGS. 1 through 4 there is shown one embodiment of a deformable gasket 1 in accordance with the present invention. FIG. 1 shows the deformable gasket 1 in perspective. The deformable gasket 1, as outlined elsewhere herein, would be made of a deformable polymeric material which could be releasably adhered to the outward surface of a wearable viewing lens 2. The viewing lens 2 might be a viewing shield of a helmet, a goggle face or the like. The deformable characteristic of the material of manufacture of the gasket 1 refers to the ability of the gasket 1, in its thickness, be stretched or to vary across the face of the gasket 1, to either accommodate surface irregularities in the lens or also to allow for a degree of stretching when the gasket is pulled away from the surface of the lens to maintain the circumferential seal established between the lens and the lens cover set.

The deformable gasket 1 is used in conjunction with the outward surface of the wearable viewing lens 2 and an adhesive lens cover set, to provide a circumferential seal between the outward surface of the wearable viewing lens 2 and the adhesive lens cover set to form a seal sufficient to block any ingress of debris or moisture between the lens cover set and the viewing lens 2. Individual disposable lens covers can be peeled off and disposed from the lens cover set when it is desired to rapidly clean the viewing surface.

The deformable gasket 1 would be shaped in relation to the wearable viewing lens 2 in respect of which it would be used—as such a custom shape deformable gasket 1 would be required for different types of viewing lenses 2, or it may in certain cases be possible to manufacture a deformable gasket 1 which had the outer shape desired or required to allow for the use of the deformable gasket 1 with a plurality of similarly shaped viewing lenses 2. Both such approaches are contemplated within the scope of the present invention.

As outlined throughout, the viewing lens 2 would include alignment means 3 to permit the alignment of a lens cover set for adhesive attachment. The alignment means 3 could comprise any number of different means of alignment of the lens cover set although it is explicitly contemplated that the alignment means 3 could comprise a plurality of retaining posts extending outwards from the forward facing surface of the viewing lens 2 which could engage corresponding holes or apertures through the lens cover set. The alignment means 3 are contemplated to be disposed on the forward outward facing surface of the viewing lens 2 in proximity to the outer circumference 4 thereof. In certain embodiments the alignment means 3 might also comprise flanges are tabs extending upwardly from the outer edge of the viewing lens 2 as well, although embodiments of the viewing lens 2 in which the alignment means 3 comprise retaining posts extending upwards and outwards there from are the likely most popular and widely available lens configurations.

The outer circumferential shape of the deformable gasket 1 will be smaller than the outer circumferential shape of the outward facing surface of the viewing lens 2, insofar as the deformable gasket 1 when attached to the viewing lens 2 will be located within the perimeter defined by the alignment means 3. The disposition of the gasket inside of the perimeter defined by the alignment means 3 around the outer circumference of the viewing lens 2, insofar as it provides a maximized seal between a lens cover set and the viewing lens 2, and the deformable nature of the gasket 1 insofar as the material of manufacture will permit the stretching and variance of thickness of the gasket 1 when pulled upon by the attached lens cover set, to allow for a maximized circumferential seal, are key aspects of the novelty of the deformable gasket of the present invention.

Figure 2:
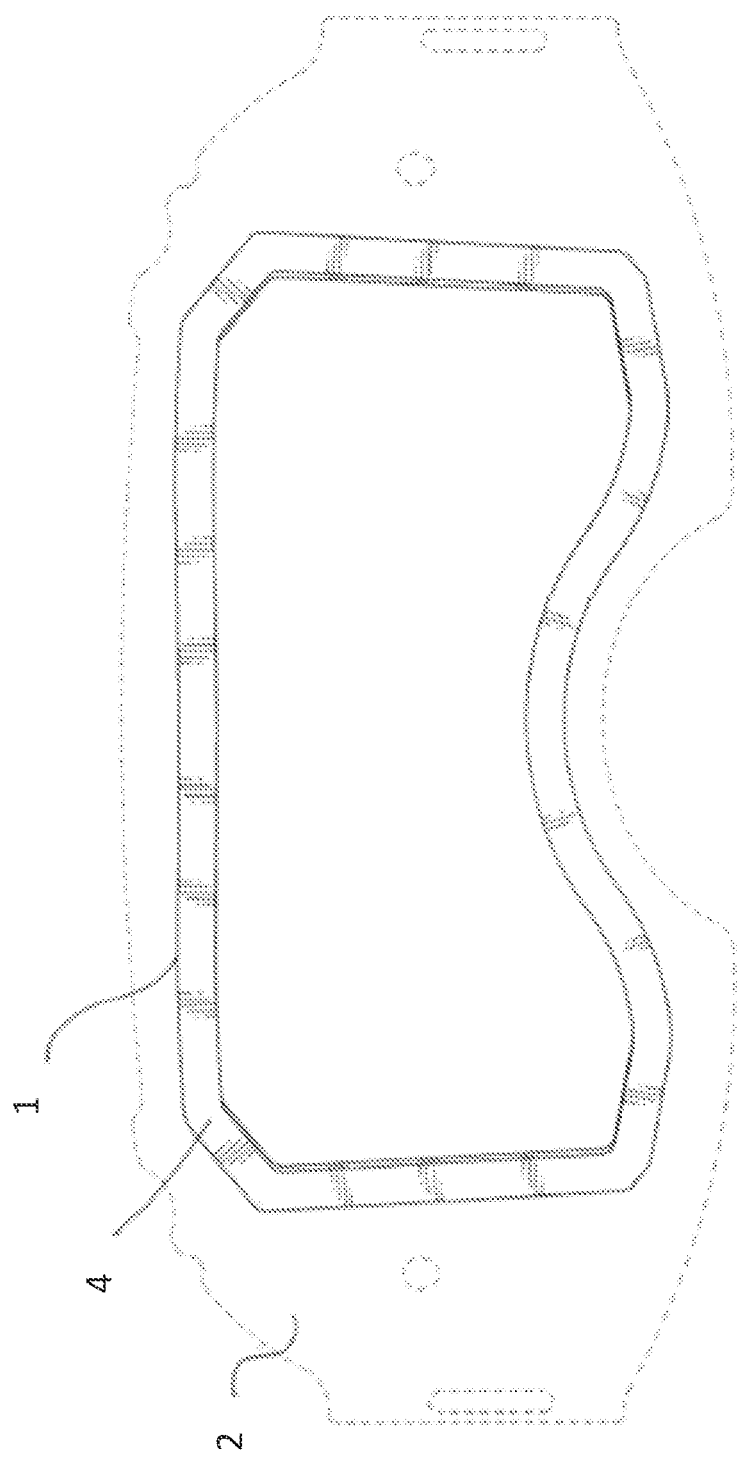
FIG. 2 is a front view of the gasket of FIG. 1.
Figure 3:
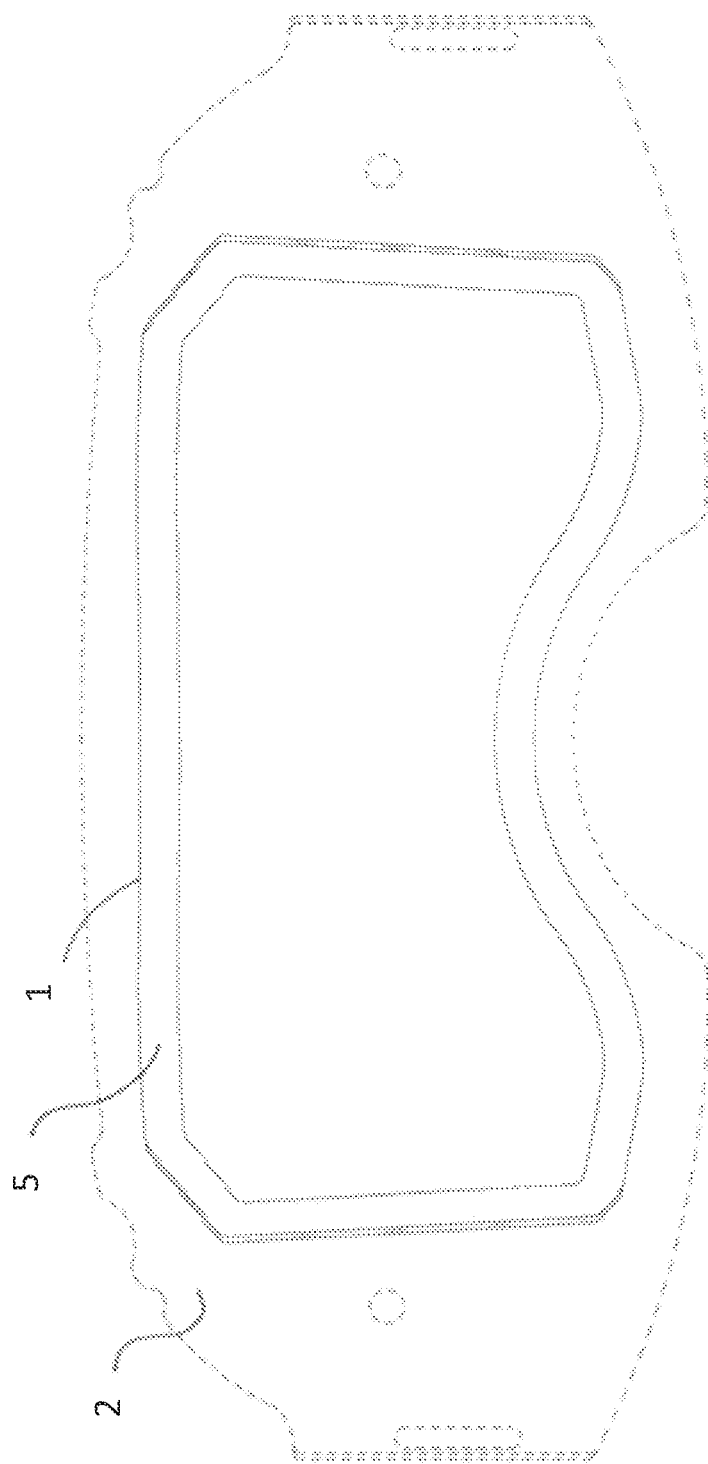
FIG. 3 is a rear view of the gasket of FIG. 1.

Referring to FIG. 2 and FIG. 3 there is shown a rear and forward view of the deformable gasket 1. FIG. 2 shows an adhesive on the rear surface 4 of the deformable gasket 1, whereas there is a nonadhesive forward facing surface 5 of the deformable gasket 1 shown in FIG. 3. As is outlined above, certain embodiments of the deformable gasket 1 might also include an adhesive surface on the forward face 5 of the deformable gasket 1 instead of the nonadhesive face 5 shown in FIG. 4. Both such approaches will be understood to be within the scope of the present invention.

The deformable thickness of the gasket 1 is also shown in FIGS. 2 and 3.

Many different materials of manufacture could be used for the deformable gasket 1. Any material that was pliant and flexible enough to be applied to the surface of an arcuate viewing lens surface and deformable enough to allow for variation and stretching of the thickness of the gasket 1 will be understood to be within the scope of the present invention. The deformable nature of the gasket 1 coupled with the exterior circumferential shape which can be attached in relation to and inside of the viewing perimeter of the lens defined by the alignment means defines the shape and material of the gasket 1. The gasket 1 will be attached to the viewing lens surface 2 using an adhesive of sufficient strength to allow for the pull away of disposable lens covers from attached lens cover set without a breach of the circumferential seal between the lens surface and the lens cover set.

The deformable gasket 1 is envisioned to be provided for sale with a nonadhesive peel-away cover on the adhesive rearward face 4, so that the deformable gasket 1 can be sold without exposure of the adhesive surface, and the adhesive rearward surface 4 can then be exposed for attachment to the viewing lens 2 when desired to do so.

It is specifically contemplated that in addition to the outer circumference and shape of the deformable gasket 1 being such that it will when adhesively applied to the viewing lens 2 be disposed inside of the perimeter 6 defined by the alignment means around the outer circumference 3 of the viewing lens 2, the adhesive on the rearward face 4 of the deformable gasket 1 will be a stronger releasable adhesive than the adhesive used between the laminated layers of the lens cover set, so that the tear-away action of removing disposable lens covers from the lens cover set during use of the wearing lens 2 will not, without undue force being applied thereon, resulted in the separation of the deformable gasket 1 from the viewing lens 2. The adhesive used on the deformable gasket 1 for attachment thereof to the viewing lens 2 will still be releasable i.e. it will still be possible to remove the deformable gasket 1 from the viewing lens 2 either for replacement thereof or removal thereof if desired.

Figure 4:
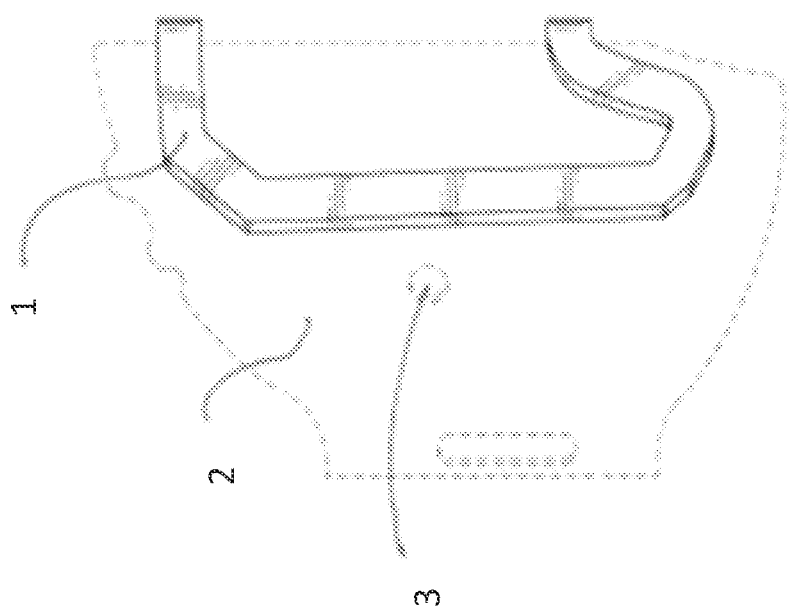
FIG. 4 is a left side of the gasket of FIG. 1 showing the attachment to an arcuate viewing lens surface.
Figure 5:
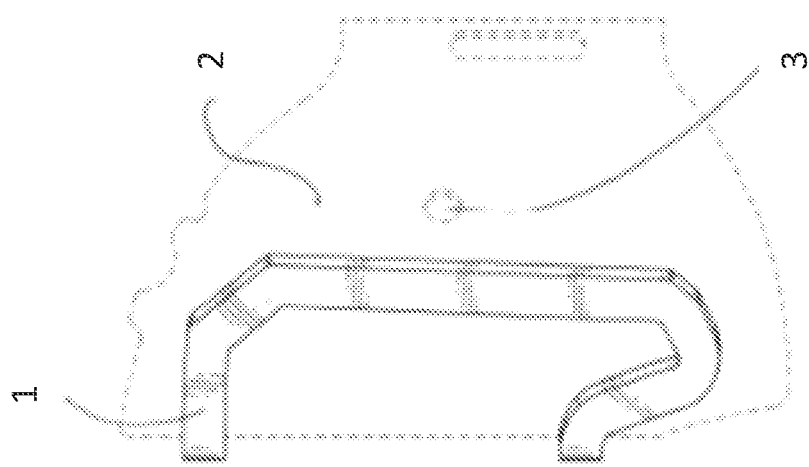
FIG. 5 is a right side view of the gasket of FIG. 1 showing the attachment to an arcuate viewing lens surface.

FIGS. 4 and 5 show left and right side views of the deformable gasket 1 in relation to an arcuate viewing lens surface 2.

Figure 6:
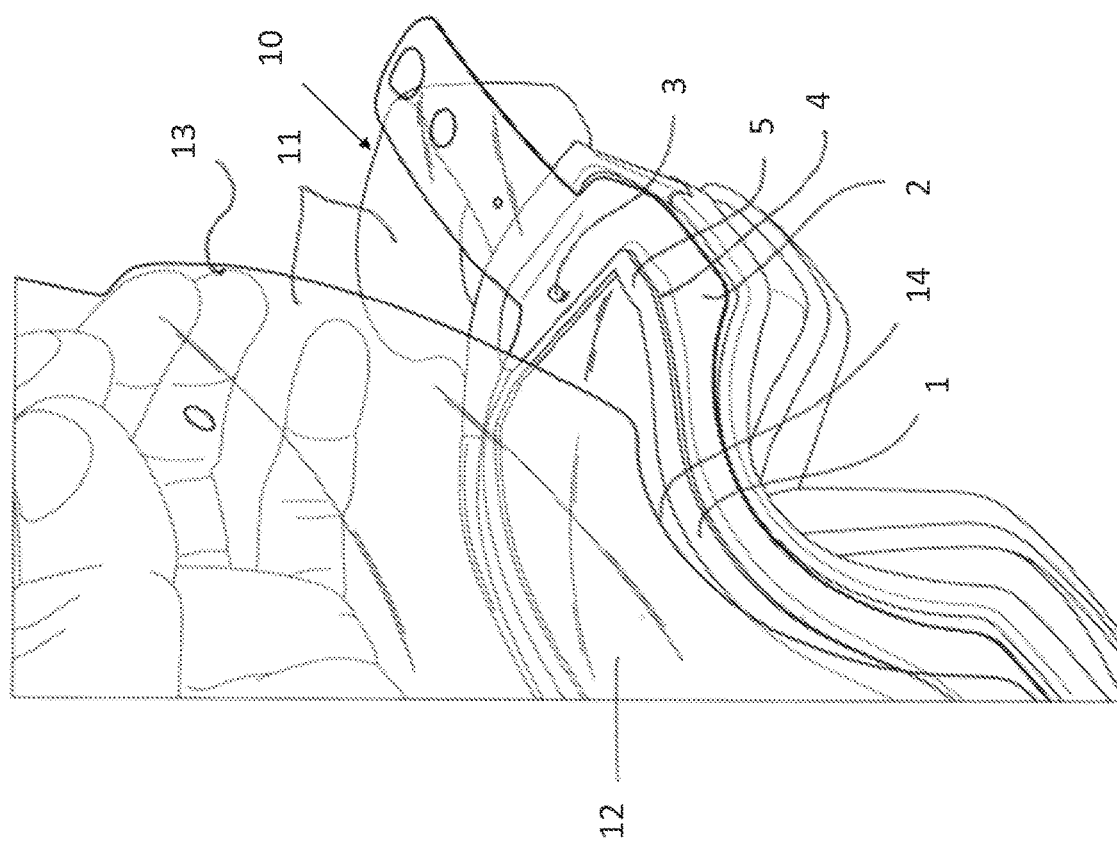
FIG. 6 is a view of a lens cover set in accordance with the invention in position on a viewing lens surface, with one of the disposal lens covers being peeled away for disposal.

Referring next to FIG. 6, there is shown a lens cover set 10 for use in conjunction with a wearable viewing lens 2 and including a deformable gasket 1 such as outlined above. The view of the FIG. shows the peeling away of a disposable lens cover 11 from the lens cover set 10.

The lens cover set 10 comprises a releasably laminated set of disposable lens covers 11. Each lens cover 11 has a outward facing surface 12 which is nonadhesive, which provides a clean outer vision surface, and an inward facing surface 13 which includes a releasable adhesive 14 which allows laminar attachment of the inward facing surface 13 to the outward facing surface 12 of an adjacent optical lens cover 11 in the lens cover set 10. The disposable lens covers 11, and the releasable adhesive 14 used on the inward facing surfaces 13 of each, are visibly transparent, such that the laminated set 10 provides unobstructed vision therethrough.

On the inward facing surface of the innermost lens cover 11 of the lens cover set 10 there is attached a deformable gasket 1 having a front surface 5 and a rear surface 4. The front surface 4 of the deformable gasket 1 is attached to the inward facing surface 13 of the inner most lens cover 11 of the lens cover set 10. The rear surface 5 of the deformable gasket 1 includes adhesive for attachment to the forward facing outer surface of the viewing lens 2. The lens cover set 10 might be manufactured for shipping and sale with a peel-away nonadhesive cover on the adhesive surface of the rear of the deformable gasket 1 which can be peeled away when the lens cover set 10 is attached to a viewing lens.

The viewing lens 2 would include alignment means 3 in proximity to the outer circumference thereof which are used to alignment the lens cover set 10 during its adhesive attachment. The alignment means 3 are contemplated in most circumstances to comprise a plurality of retaining posts reaching outwards from the forward surface of the viewing lens. The lens cover set 10 would include a plurality of corresponding apertures through which the retaining posts could extend—in attachment of the lens cover set 10 to the viewing lens 2, the lens cover set 10 would be aligned with the retaining posts such that they would extend through these apertures allowing for the guidance of the lens cover set 10 into the appropriate adhesive attachment position on the outward surface of the viewing lens 2.

The shape and size of the lens cover set 10 will be such that the disposable lens covers 11 would cover the entirety of the viewing area of the viewing lens 2 and extend outside of the alignment means 3. The positioning of the deformable gasket 1 inside of the perimeter defined by the alignment means 3 will maximize the integrity of the circumferential seal provided thereby.

The releasable adhesive used between the disposable lens covers 11 would purposely be a weaker releasable adhesive than that used to attach the deformable gasket 1 to the lens cover 2. Removal of the lens covers 11 from the set 10 would then be least likely to result in the unintended peeling away of the deformable gasket 1 from the lens cover 2, maximizing the likelihood of maintaining the seal between the lens cover set 10 and the lens itself 2 and lessening the likelihood of the ingress of any debris or moisture between the lens cover set 10 and the lens 2. It is specifically contemplated that these products would be used in rugged outdoor high debris and high moisture applications such as motocross riding and the like, allowing for the rapid cleaning of a viewing lens by the peel-away of a lens cover 11 during a race or the like.

In its use, the lens cover set 10 would permit for the rapid cleaning of the viewing surface of the viewing lens 2 by the peel-away and disposal of the disposable lens cover 11 therefrom. By gripping and removing one of the disposable lens covers 11, a fresh lens cover 11 would be exposed, by its nonadhesive outer surface. Insofar as the adhesive attaching the deformable gasket 1 to the viewing lens 2 is stronger than the laminating adhesive between the lens cover 11 layers, so long as excessive force was not used, the likelihood of breaching the circumferential seal provided by the deformable gasket 1 is minimized.

FIG. 6 also shows an operator peeling away one of the disposable lens covers 11, demonstrating the operation of the lens cover set 10.

It will be apparent to those skilled in the art that many more modifications besides those already described are possible without departing from the inventive concepts herein. For example, it will be realized that the optimal dimensions for the various parts of the invention, materials, shape, form, manner of assembly, and operation or use will be apparent to those of skill in the art. The inventive subject matter, therefore, is not to be restricted except in the scope of any claims as may be directed to the disclosure presented herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. All suitable modifications and equivalents that may be resorted to are thereby considered to be within the scope of the present invention.

The invention claimed is:

1. A gasket for use to provide enhanced adhesive attachment of a lens cover set to a wearable viewing lens, wherein:
   an outward surface of the viewing lens includes alignment means extending outwards therefrom in proximity to an outer circumference of the viewing lens to facilitate the alignment of the lens cover set in relation to the viewing lens, the alignment means defining a viewing perimeter;
   each lens cover of the lens cover set being adhesively laminated and disposable, each of which has an outward-facing surface that is non-adhesive to provide a clean outer vision surface and an inward-facing surface including a releasable adhesive having an adhesion value permitting the peel-away removal of the lens covers from each other; and:
      the inward facing surface of the innermost disposable lens cover of the lens cover set permits adhesive attachment of the lens cover set to the outward surface of the viewing lens, and the remainder of the plurality of disposable lens covers are adhesively laminated together by attachment of their inward-facing adhesive surfaces to the non-adhesive outward-facing surface of adjacent lens covers;
      the lens cover set is of a size approximately corresponding to the outer circumference of the lens;
      the combination of the disposable lens covers and laminating adhesive comprising the lens cover set are clear, such that the combination of the lens cover set when attached to the lens permits a viewer to see therethrough;
      the lens cover set engages the alignment means to permit alignment of the lens cover set to the viewing lens during any adhesive attachment step; and
      the disposable lens covers of the lens cover set are removeable for disposal when the visibility therethrough is impaired; and
   the gasket includes a material of deformable thickness permitting stretching and variation in the thickness of the gasket and having a front surface and rear surface, wherein:
      an outer circumference of the rear surface of the gasket includes a releasable adhesive for attachment to the outward surface of the viewing lens;
      the front surface of the gasket permits adhesive engagement of the inward-facing adhesive surface of the innermost disposable lens cover of the lens cover set to provide a circumferential seal between the lens cover set and the viewing lens preventing the entry of moisture or debris between the lens cover set and the viewing lens; and
      the gasket is sized and shaped to fit within the viewing perimeter, such that the circumferential seal created by the gasket between the lens cover set and the viewing lens is positioned inside of the alignment means; and
   wherein the adhesion value of the releasable adhesive used to attach the gasket between the lens cover set and the viewing lens is higher than the adhesion value of the laminating adhesive between the disposable lens covers of the lens cover set, whereby the gasket is configured to not pull away from the surface of the viewing lens when the laminated disposable lens covers are removed from the front of the lens; and
   when the front surface of the gasket is pulled on in a pulling force by an adhesively attached lens cover set, the thickness of the gasket will deform, maintaining the circumferential seal until the pulling force is sufficient to release the lens cover set from the front surface of the gasket.

2. The gasket of claim 1, wherein the viewing lens comprises a viewing helmet shield.

3. The gasket of claim 1, wherein the viewing lens comprises a goggle lens.

4. The gasket of claim 1, wherein the alignment means comprises retaining posts configured to engage corresponding apertures extending through the lens cover set.

5. The gasket of claim 1, wherein the disposable lens covers include non-adhesive gripping means for manual gripping and adhesive release thereof from the lens cover set.

6. The gasket of claim 1, further comprising a removable non-adhesive protective covering removably attached to the adhesive rear surface of the gasket.

7. A lens cover set for use on an outward surface of a viewing lens including alignment means extending outwards therefrom in proximity to an outer circumference of the viewing lens to facilitate the alignment of the lens cover set in relation to the viewing lens, the alignment means defining a viewing perimeter, and the lens cover set comprising:
   a plurality of lens covers each being adhesively laminated, disposable, and having an outward-facing surface that is non-adhesive to provide a clean outer vision surface and an inward-facing surface including a releasable adhesive having an adhesion value permitting the peel-away removal of the lens covers from each other for disposal when the visibility therethrough is impaired, and the inward-facing surface of the innermost disposable lens cover of the lens cover set providing adhesive attachment of the lens cover set to the outward surface of the viewing lens, and the remainder of the plurality of lens covers are adhesively laminated together by attachment of their inward-facing adhesive surfaces to the non-adhesive outward-facing surface of adjacent lens covers; and a gasket comprising a material of deformable thickness configured to permit stretching and variation in the thickness of the gasket and having a front surface and rear surface, wherein:

an outer circumference of the rear surface of the gasket includes a releasable adhesive for attachment to the outward surface of the viewing lens;

the front surface of the gasket is adhesively attached to the inward-facing adhesive surface of the innermost disposable lens cover of the lens cover set to provide a circumferential seal between the lens cover set and the viewing lens preventing the entry of moisture or debris between the lens cover set and the viewing lens; and the gasket is sized and shaped to fit within the viewing perimeter, such that the circumferential seal created by the gasket between the lens cover set and the viewing lens is positioned inside of the alignment means;

wherein:

the lens cover set is of a size approximately corresponding to the outer circumference of the viewing lens;

the combination of the disposable lens covers and laminating adhesive comprising the lens cover set are clear, such that the combination of the lens cover set when attached to the viewing lens permits a viewer to see therethrough;

the adhesion value of the releasing adhesive used to attach the gasket between the lens cover set and the viewing lens is higher than the adhesion value of the laminating adhesive between the disposable lens covers of the lens cover set, whereby the gasket will not pull away from the surface of the viewing lens when the laminated disposable lens covers are removed from the front of the lens; and when the front surface of the gasket is pulled on in a pulling force by an adhesively attached lens cover set, the thickness of the gasket will deform, maintaining the circumferential seal until the pulling force is sufficient to release the lens cover set from the front surface of the gasket.

8. The lens cover set of claim 7, wherein the viewing lens comprises a viewing helmet shield.

9. The lens cover set of claim 7, wherein the viewing lens comprises a goggle lens.

10. The lens cover set of claim 7, further comprising a removable adhesive cover on the rear surface of the gasket configured to protect the adhesive around the circumference thereof until removal of the cover for attachment of the lens cover set to the viewing lens.

11. The lens cover set of claim 7, wherein the alignment means on the viewing lens comprises retaining posts to engage corresponding apertures through the lens cover set, for alignment of the lens cover set, the retaining posts being located sufficiently inside the outer circumference of the front vision surface of the viewing lens to permit the gaskets circumferential sealing attachment therearound in proximity to the outer circumference of said front vision surface.

12. The lens cover set of claim 7, wherein the optical lens covers include non-adhesive gripping means for manual gripping and removal thereof from the set.

13. The lens cover set of claim 7, wherein the alignment means extend sufficiently forward from the viewing lens to permit the stacked attachment of multiple lens cover sets.

* * * * *